United States Patent [19]

Fukusaki et al.

[11] Patent Number: 5,677,155
[45] Date of Patent: Oct. 14, 1997

[54] **PROCESS FOR PREPARING THE SEX PHEROMONE OF *LYMANTRIA DISPAR* L**

[75] Inventors: Eiichiro Fukusaki; Tetsuo Omata; Shuji Senda, all of Osaka, Japan

[73] Assignee: Nitto Denko Co., Ltd., Ibaraki, Japan

[21] Appl. No.: 547,926

[22] Filed: Oct. 25, 1995

[30] Foreign Application Priority Data

Nov. 4, 1994  [JP]  Japan .................................. 6-295891

[51] Int. Cl.$^6$ ........................ C12P 7/00; C12N 9/14; C12N 9/20
[52] U.S. Cl. ................. 435/132; 435/177; 435/195; 435/197; 435/198; 435/123; 435/155; 435/280
[58] Field of Search ........................... 435/132, 123, 435/198, 280, 155, 197, 177, 195

[56] References Cited

U.S. PATENT DOCUMENTS

| | | | |
|---|---|---|---|
| 4,471,130 | 9/1984 | Katsuki et al. | 556/54 |
| 4,732,853 | 3/1988 | Whitesides et al. | 435/123 |
| 4,923,810 | 5/1990 | Walts et al. | 435/117 |
| 4,996,158 | 2/1991 | Oda et al. | 435/280 |
| 5,213,975 | 5/1993 | Fukusaki et al. | 435/123 |
| 5,463,149 | 10/1995 | Fukumoto et al. | 570/135 |

OTHER PUBLICATIONS

Vig et al. Indian J. Chem. vol. 24B, 1985 pp. 860–861.
Chan et al. J. Organometallic Chem. vol. 285 pp. 109–119 1985.

*Primary Examiner*—Blaine Lankford
*Assistant Examiner*—Christopher R. Tate
*Attorney, Agent, or Firm*—Armstrong, Westerman, Hattori, McLeland & Naughton

[57] ABSTRACT

A process for preparing the sex pheromone of *Lymantria dispar* L. effectively which comprises the steps of reacting 1-bromodecane and propargyl alcohol tetrahydropyranylether in the presence of sodium hydroxide to give 1-tetrahydropyranyloxy-2-tridecyne, treating the tetrahydropyranyloxy-2-tridecyne with p-toluenesulfonic acid to give 2-tridecyn-1-ol, catalystic-hydrogenating the 2-tridecyn-1-ol in the presence of Lindlar catalyst to give (Z)-2-tridecen-1-ol, oxidizing the (Z)-2-tridecen-1-ol with peroxide to give (±)-cis-2,3-epoxy-1-tridecanol, reacting the (±)-cis-2,3-epoxy-1-tridecanol with acid anhydride in the presence of hydrolase in an organic solvent for a stereoselective acylation and recovering unreacted optically active (2R, 3S)-cis-2,3-epoxy-1-tridecanol after the acylation, reacting the optically active (2R, 3S)-cis-2,3-epoxy-1-tridecanol with toluenesulfonylchloride to give (2R, 3S)-cis-1-p-toluenesulfoxy-2,3-epoxytridecane, and reacting the (2R, 3S)-cis-1-p-toluenesulfoxy-2,3-epoxytridecane with di(4-methylpentyl) lithium copper reagent to yield (7R, 8S)-cis-2-methyl-7,8-epoxyoctadecane which is the sex pheromone of *Lymantria dispar* L.

12 Claims, 12 Drawing Sheets

※ 1: TETRAHYDROPYRANYLOXY
※ 2: m-CHLOROPERBENZOIC ACID
※ 3: p-TOLUENESULFONYLCHLORIDE

RESULT OF QUANTITATIVE CALCULATION

| CH | PKNO | TIME | AREA | HEIGHT | MK | IDNO | CONC | NAME |
|---|---|---|---|---|---|---|---|---|
| 1 | 6 | 5.838 | 2779 | 1246 | | | 0.6643 | |
| | 7 | 6.442 | 2192 | 1255 | | | 0.5241 | |
| | 11 | 7.187 | 1014 | 521 | V | | 0.2424 | |
| | 16 | 9.192 | 1313 | 360 | V | | 0.3139 | |
| | 17 | 10.272 | 1169 | 338 | | | 0.2795 | |
| | 19 | 10.49 | 6542 | 2268 | | | 1.564 | |
| | 20 | 10.953 | 403278 | 71459 | S | | 96.412 | |
| | | TOTAL | 418286 | 77447 | | | 100 | |

RESULT OF QUANTITATIVE CALCULATION

| CH | PKNO | TIME | AREA | HEIGHT | MK | IDNO | CONC | NAME |
|---|---|---|---|---|---|---|---|---|
| 1 | 1 | 3.769 | 871 | 336 | | | 0.065 | |
| | 3 | 5.894 | 6240 | 2675 | S | | 0.4659 | |
| | 5 | 7.155 | 1190 | 490 | | | 0.0889 | |
| | 8 | 7.967 | 511 | 219 | V | | 0.0382 | |
| | 13 | 9.127 | 1273 | 498 | | | 0.0951 | |
| | 16 | 10.348 | 2050 | 655 | | | 0.153 | |
| | 17 | 10.412 | 2798 | 710 | V | | 0.2089 | |
| | 18 | 10.638 | 14505 | 1588 | V | | 1.083 | |
| | 19 | 11.199 | 1307938 | 125936 | SV | | 97.6521 | |
| | 25 | 12.852 | 718 | 233 | V | | 0.0536 | |
| | 26 | 12.949 | 607 | 164 | V | | 0.0453 | |
| | 29 | 13.234 | 684 | 258 | V | | 0.051 | |
| | | TOTAL | 1339385 | 133760 | | | 100 | |

```
CAL. METHOD    00
               SF              PA              PB
     .100000 10+03    .100000 10+01    .100000 10+01

NO.   NAME      RT      A OR H      MK      CONC
 1              9.364      40800            3.2551
 2             10.324     603608           48.1572
 3             13.710     609003           48.5876

TOTAL              1253412           100.0000
```

```
CAL. METHOD    00
                    SF              PA              PB
         .100000 10 +03    .1000000 10 +01    .1000000 10 +01

NO.   NAME      RT       A OR H      MK       CONC
 1              8.370      7693               0.1200
 2             10.344   6398155              99.8799

TOTAL            6405848              100.0000
```

CHROMATOPAC C-R4A    CH=1    REPORT NO. = 4    CHROMATO = 1 :⊇CHRMI. COO

RESULT OF QUANTITATIVE CALCULATION

| CH | PKNO | TIME | AREA | HEIGHT | MK | IDNO | CCNC | NAME |
|---|---|---|---|---|---|---|---|---|
| 1 | 1 | 3.464 | 2862 | 1800 | | | 0.9064 | |
| | 2 | 6.011 | 1687 | 783 | | | 0.5343 | |
| | 3 | 6.083 | 2573 | 445 | V | | 0.8147 | |
| | 6 | 15.548 | 1973 | 990 | | | 0.6249 | |
| | 12 | 16.413 | 305919 | 71709 | SV | | 96.8702 | |
| | 14 | 22.187 | 788 | 144 | | | 0.2496 | |
| | | TOTAL | 315803 | 75872 | | | 100 | |

PROCESS FOR PREPARING THE SEX PHEROMONE OF *LYMANTRIA DISPAR L.*

FIELD OF THE INVENTION

This invention relates to a process of preparing the sex pheromone of *Lymantria dispar L.* The object of the invention is to provide a superior process generally used as an industrial manufacturing process without many steps for preparing at a high yield the sex pheromone of *Lymantria dispar L.* which can attract one kind of forest pest, *Lymantria dispar L.*.

PRIOR ART

*Lymantria dispar L.* is one important kind of noxious insects which spoils forests and shades of trees by eating trees throughout the northeast of the United States and the other world. Larvae and imagoes of *Lymantria dispar L.* are known also in Japan and do damage to fruit trees of apples, pears, peaches and so on, and trees such as willows and Japanese oaks. As a method for control of the forest pest, a great deal of attention is being paid to a method using pheromone which does no harm to men and animals, and the environment.

As known methods of preparing the sex pheromone of *Lymantria dispar L.*, Bryant E. Rossiter et al. have proposed a method by synthesis which is characterized in asymmetric epoxidation of allyl alcohol (J. Am. Chem. Soc., vol. 103, 464, (1981)), and Daniel Bianchi et al. have proposed a method by synthesis which is characterized in synthesis of optically active epoxy alcohol by means of transesterification of racemic epoxy alcohol and acetate with lipase (Tetrahedron Letters vol. 29,2455, (1988)).

The present inventors have also proposed a method of preparing optically active epoxy alcohol comprising the steps of adding carboxylic anhydride to racemic epoxy alcohol in the presence of a hydrolase to esterify (−)-form of the epoxy alcohol preferentially, separating optically active epoxy ester from optically active epoxy alcohol and hydrolyzing the optically active epoxy ester to yield optically active epoxy alcohol (Japanese patent application no. hei3-170625).

Problem to be Solved by the Invention

The above mentioned methods have not solved the problem that the yield of the objective sex pheromone of *Lymantria dispar L.* is insufficient. Therefore the present invention has the object to provide a process for preparing at a higher yield the sex pheromone of *Lymantria dispar L.* which can efficiently control one important kind of forest pest, *Lymantria dispar L.*.

SUMMARY OF THE INVENTION

The object of the present invention is to solve said problem, and according to a process of claim 1 of the invention (7R,8S)-cis-2-methyl-7,8-epoxyoctadecane which is the sex pheromone of *Lymantria dispar L.* can be obtained by reacting 1-bromodecane and propargyl alcohol tetrahydropyranylether in the presence of sodium hydroxide to give 1-tetrahydropyranyloxy-2-tridecyne, treating the 1-tetrahydropyranyloxy-2-tridecyne with p-toluenesulfonic acid to give 2-tridecyn-1-ol, catalystic-hydrogenating the 2-tridecyn-1-ol in the presence of Lindlar catalyst to give (Z)-2-tridecen-1-ol, oxidizing the (Z)-2-tridecen-1-ol, with a peroxide to give (±)-cis-2,3-epoxy-1-tridecanol, reacting the (±)-cis-2,3-epoxy-1-tridecanol with acid anhydride in the presence of a hydrolase in an organic solvent to give stereoselective acylation, recovering unreacted optically active (2R,3S)-cis-2,3-epoxy-1-tridecanol, reacting the optically active (2R,3S)-cis-2,3-epoxy-1-tridecanol with p-toluenesulfonylchloride to give (2R,3S)-cis-1-p-toluenesulfoxy-2,3-epoxytridecane, and reacting the (2R,3S)-cis-1-p-toluenesulfoxy-2,3-epoxytridecane with di(4-methylpentyl) lithium copper reagent.

DETAILED DESCRIPTION OF THE INVENTION

Figure 1:
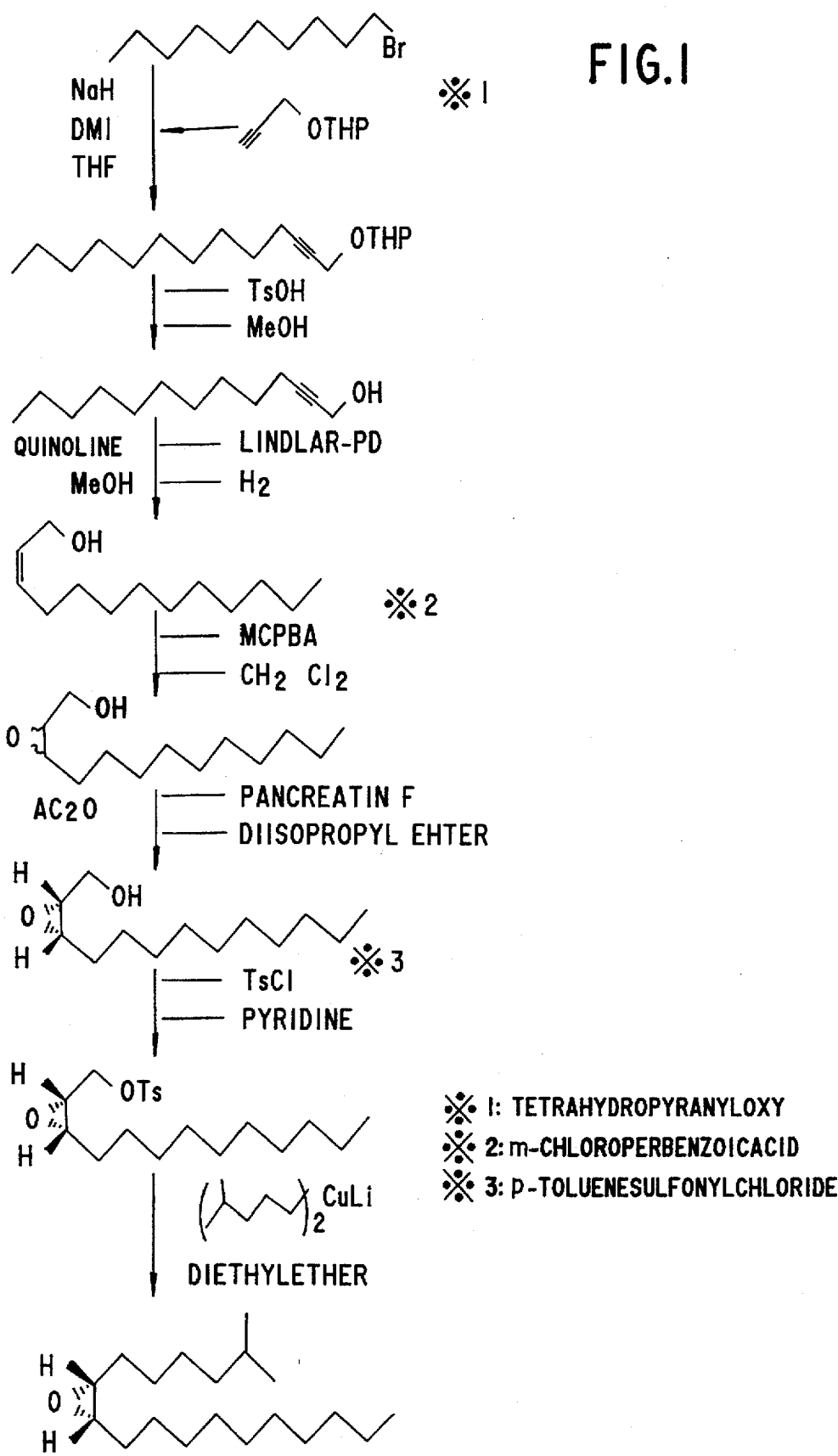
FIG. 1 is a chart showing reaction scheme of a process for preparing the sex pheromone of *Lymantria dispar L.* relating to the present invention.

A process for preparing the sex pheromone of *Lymantria dispar L.* relating to the present invention will be described in detail hereinafter.

In the 1st step of the invention, 1-tetrahydropyranyloxy-2-tridecyne (formula 12) is synthesized by using 1-bromodecane (formula 10) and propargyl alcohol tetrahydropyranylether (formula 11) as the starting materials and reacting the starting materials in the presence of sodium hydroxide.

 (formula 10)

 (formula 11)

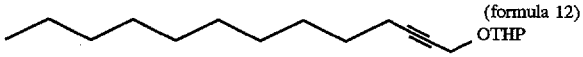 (formula 12)

It is favorable to perform this reaction at room temperature or above under a current of inert gas. When solvent is used for the reaction, any solvent can be used unless it prevents the reaction. To put it concretely, tetrahydrofuran, dimethylformamide, toluene, chlorobenzene, chloroform, carbon tetrachloride, methanol and so on can be favorably used.

The ratio of 1-bromodecane: propargyl alcohol tetrahydropyranylether is preferably about 1:0.5–1.0 in mole ratio.

The amount of sodium hydroxide is favorably about ¼–⅓ parts by weight per 1 part by weight of propargyl alcohol tetrahydropyranylether. It is not favorable to use sodium hydroxide of which the amount is less than ¼ parts by weight per 1 part by weight of propargyl alcohol tetrahydropyranylether, because 1-tetrahydropyranyloxy-2-tridecyne can not be effectively synthesized. While it is not favorable either to use sodium hydroxide of which the amount is more than ⅓ parts by weight, because remained unreacted sodium hydroxide should be disposed.

After the reaction, the reactant including crude 1-tetrahydropyranyloxy-2-tridecyne is vacuum-concentrated to proceed to the 2nd step.

In the 2nd step, the crude 1-tetrahydropyranyloxy-2-tridecyne obtained in the 1st step is reacted with p-toluenesulfonic acid to give 2-tridecyn-1-ol (formula 13).

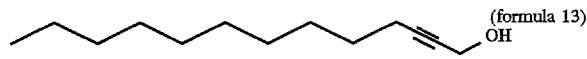
(formula 13)

The amount of p-toluenesulfonic acid to be used is preferably 0.5–1.5% by weight of the amount of 1-tetrahydropyranyloxy-2-tridecyne.

It is not favorable to use p-toluenesulfonic acid of which the amount is less than 0.5% by weight of tile amount of 1-tetrahydropyranyloxy-2-tridecyne, because the reaction can not be effectively proceeded. While it is not favorable either to use p-toluenesulfonic acid of which tile amount is more than 1.5% by weight, because it is difficult to remove p-toluenesulfonic acid after the reaction.

The reaction is kept for about 2–24 hours at room temperature. Thus obtained reactant including crude 2-tridecyn-1-ol is vacuum-concentrated to proceed to the 3rd step.

In the 3rd step, the obtained crude 2-tridecyn-1-ol is catalystic-hydrogenated in the presence of Lindlar catalyst to synthesize (Z)-2-tridecen-1-ol (formula 14).

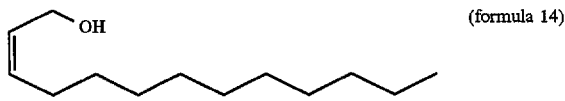
(formula 14)

The catalystic-hydrogenation is performed by reacting liquid phase of the 2-tridecyn-1-ol to be reduced, Lindlar catalyst and solvent with hydrogen gas at about 0–15° C.

It is favorable to use Lindlar catalyst of which the amount is about 0.02–0.05% by weight of the amount of 2-tridecyn-1-ol to be reduced, and to use solvent which does not prevent the reaction, for example, methanol and so on.

Lindlar catalyst is especially used for the 3rd step since the use of Lindlar catalyst produces a fast reduction by catalystic hydrogenation so that it is most suitable for an industrial process.

The reactant is vacuum-concentrated to proceed to the 4th step.

In the 4th step, the crude (Z)-2-tridecen-1-ol obtained by the catalystic hydrogenation is oxidized with a peroxide to give (±)-cis-2,3-epoxy-1-tridecanol (formula 15)

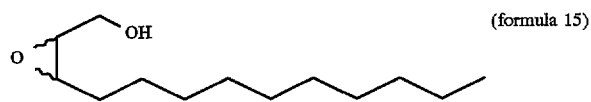
(formula 15)

As for the peroxide, m-chloroperbenzoic acid, monomagnesium monoperphthalate, t-buytl peroxide and so on can be suitably used, especially, m-chloro perbenzoic acid is most preferably used in view of the yield and the reactivity.

The amount of peroxide is preferably about 0.8–1.5 times the weight of (Z)-2-tridecen-1-ol. The oxidation is kept for about 12–17 hours at room temperature.

After time reaction, the reacted solution is separated into an organic layer and a water layer to be washed, and thus obtained (±)-cis-2,3-epoxy-1-tridecanol is crystallized to proceed to the 5th step.

In the 5th step, the (±)-cis-2,3-epoxy-1-tridecanol obtained in the 4th step is reacted with acid anhydride as a donor of acyl in the presence of a hydrolase in an organic solvent to give a stereoselective acylation.

As for the hydrolase, any lipase can be used such as a lipase derived from pancreas of pig, bacteria, yeast or mold, however, a lipase derived from pancreas of pig is most preferably used. Either purified or crude enzymes can be used for the reaction, and there is no particular restriction on the state of the enzymes, therefore any state such as powder, grain or dried biomass microorganism (treated biomass and paused biomass) containing the enzyme can be used. These enzymes can be used as they are, or immobilized on a carrier. Moreover after the reaction, it is possible to re-use the recovered enzymes.

The organic solvent favorably used for the stereoselective acylation in the 5th step can be any non-aqueous solvent. To put it concretely, any solvent which can solve the subject may be favorably used without any restriction, for example a chain aliphatic hydrocarbon solvent such as n-hexane, n-heptane, n-octane, or isooctane, a cyclic aliphatic hydrocarbon solvent such as cyclopentane or cyclohexane, a halogenated hydrocarbon solvent such as dichloromethane, trichloromethan or carbon tetrachloride, an aromatic hydrocarbon solvent such as benzene, toluene or xylene, or an ether group solvent such as diethylether, diisopropylether, n-butylether. Especially, diisopropylether is most favorably used since the objective unreacted material can be efficiently recovered.

The acid anhydrides preferably used in the 5th step are any acid anhydrides with 2–20 carbon atoms. Examples of the preferable acid anhydrides are chain carboxylic anhydrides such as acetic anhydride, propionic anhydride, butyric anhydride, valeric anhydride or capronic anhydride, and cyclic carboxylic anhydrides such as succinic anhydride or glutaric anhydride, however, it is most favorable to use acetic anhydride for facilitating the reaction.

The temperature for the stereoselective acylation is preferably within the active temperature for the hydrolase and ordinarily it is the range from 0° to 70° C., more preferably within the range from 15° to 50° C.

The ratio of combination of acid anhydride (acyl group donor): (±)-cis-2,3-epoxy-1-tridecanol is 1: not less than 0.5 in mole ratio.

(R)- optically active substance is preferentially acylated by the stereoselective acylation of (±)-cis-2,3-epoxy-1-tridecanol to give cyanoester, while optically active (2R,3S)-cis-2,3-epoxy-1-tridecanol (formula 16) which remains unreacted after the stereoselective acylation in the 5th step is recovered to proceed to 6th step.

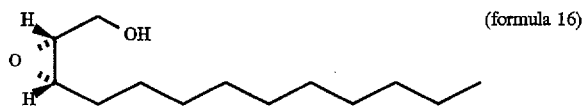
(formula 16)

Examples of this recovery process are extraction by using organic solvent being slightly soluble in water or using two solvents being an insoluble organic solvent and water as a two layer system and distillation.

In the 6th step, the optically active (2R,3S)-cis-2,3-epoxy-1-tridecanol is reacted with p-toluenesulfonylchloride to synthesize (2R,3S)-cis-1-p-toluenesulfoxy-2,3-epoxytridecane (formula 17).

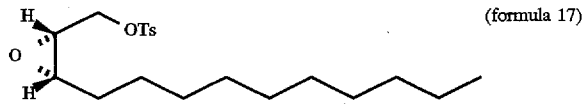
(formula 17)

In the reaction, the ratio of combination of optically active (2R,3S)-cis-2,3-epoxy-1-tridecanol: p-toluenesulfonylchloride is 1:0.8–2.0 in mole ratio. The objective (2R,3S)-cis-1-p-toluenesulfoxy-2,3-epoxytridecane can not be sufficently synthesized when the ratio of optically active (2R,3S)-cis-2,3-epoxy-1-tridecanol is less than 0.8 to 1 of p-toluenesulfonylchloride, while the danger that epoxy group may be attacked increases when the ratio is more than 2.0, so that both of the cases are not favorable.

The reaction is kept at freezing temperature for about 4–8 hours in the presence of the solvent, such as pyridine or benzoyl chloride, which does not prevent the reaction.

After the reaction, the reactant is washed and purified by means of silica gel column chromatography to recover the objective (2R,3S)-cis-1-p-toluenesulfoxy-2,3-epoxytridecane to proceed to the 7th step.

In the 7th Step, the recovered (2R,3S)-cis-1-p-toluenesulfoxy-2,3-epoxytridecane with di(4-methlpentyl) lithium copper reagent to yield the sex pheromone of *Lymantria dispar* L., namely (7R,8S)-cis-2-methyl-7,8-epoxyoctadecane (formula 18).

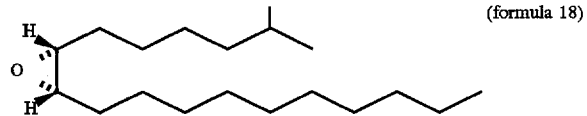
(formula 18)

To give the di(4-methlpentyl) lithium copper used in the 7th step, 4-methylpentyllithium obtained by reacting lithium with 1-bromo-4-methylpentane is reacted with copper iodide at temperature controlled under −15° C. in the presence of inert gas.

In the reaction, the ratio of combination of (2R,3S)-cis-1-p-toluenesulfoxy-2,3-epoxytridecane: di(4-methylpentyl) lithium copper is 1:1.0–1.5 in mole ratio. The objective (7R,8S)-cis-2-methyl-7,8-epoxyoctadecane can not be sufficently synthesized when the ratio of di(4-methylpentyl) lithium copper is less than 1.0 to 1 of (2R,3S)-cis-1-p-toluenesulfoxy-2,3-epoxytridecane while the danger that epoxy group may be attacked increases when the ratio is more than 1.5, so that both of the cases are not favorable.

The reaction is kept at temperature within the range from −60° to −50° C. in a current of inert gas such as argon and nitrogen.

After the reaction, the reactant is washed and purified by means of silica gel chromatography and so on to recover the objective (7R,8S)-cis-2-methyl-7,8-epoxyoctadecane.

The reaction scheme of the above mentioned 1st through 7th steps is shown in FIG. 1.

Embodiment

The present invention will now be described more concretely in detail by the following embodiment.
(Step 1)

Synthesis of 1-tetrahydropyranyloxy-2-tridecyne

As a reaction apparatus for stirring with a magnetic stirrer, a thermometer, an isobaric dropping funnel and a Dimroth condenser to which a three way stop-cock was mounted at the upper portion were mounted to a 2 L. four neck distillation flask, an argon baloon being mounted to the stop-cock.

29.7 g (net 17.5 g; 728 mmol) of sodium hydroxide (60%) was put into the apparatus to be substituted with argon. After dry THF (1 L.) was added thereto and heated for reflux for 30 minutes, propargyl alcohol tetrahydropyranylether (97 g; 693 mmol) was dropped into the apparatus for 15 minutes and then was still heated for reflux for 1hour.

1-bromodecane (161 g; 728 mmol) was solved in dry DMI (100 ml) and dropped for 30 minutes, and then was heated for reflux for 3 hours.

After disappearance of the raw materials was confirmed by means of TLC (hexane.ethyl acetate=10:1), the reactant was cooled to 5° C. and then 100 ml of water was dropped thereto for 30 minutes in a current of argon. After the drop was finished, the reactant was vacuum-concentrated, and 2 L. of ether was added and washed with water. After the reactant was washed by saturated brine and dried with magnesium sulfuric anhydride, the reactant was vacuum-concentrated to give crude 1-tetrahydropyranyloxy-2-tridecyne.
(Step 2)

Synthesis of 2-tridecyn-1-ol

A thermometer was mounted to a 2 L. four neck distillation flask for stirring with a magnetic stirrer.

Crude 1-tetrahydropyranyloxy-2-tridecyne (236 g; 693 mmol) obtained in the 1st step was solved in 1.5 L. of methanol and put into the flask, and p-toluenesulfonic acid hydrate (1.5 g; 8 mmol) was added thereto and stirred for 30 minutes at room temperature. After the stirring was stopped, the reaction was still kept for 16 hours at room temperature.

After disappearance of the raw materials was confirmed by means of TLC (hexane.ethyl acetate=10:1), 5 g of potassium carbonate solved in 50 ml of water was added thereto and stirred for 10 minutes at room temperature.

After the reactant was vacuum-concentrated, the concentrate was solved in 2 L. of ether and washed with water and then with saturated brine. After the solution was dried with magnesium sulfuric anhydride, the solution was vacuum-concentrated to give crude 2-tridecyn-1-ol.
(Step 3)

Synthesis of (Z)-2-tridecen-1-ol

As a reaction apparatus for three one motor stirring, a thermometer, a bubbler and a Liebig condenser to which a three way stop-cock was mounted at the upper portion were mounted to a 5 L. four neck distillation flask, an argon baloon being mounted to the stop-cock.

5 g of Pb-barium sulfate (5%), 5 ml of distillated quinoline and 1.5 L. of methanol were respectively put into the apparatus, and methanol solution (500 ml) of the above obtained crude 2-tridecyn-1-ol (188 g; 693 mmol) was added thereto and stirred. The reactant was substituted with argon and then with hydrogen, and was still stirred at 5°–10

° C. When a hydrogen baloon got deflated, hydrogen was filled thereto to keep the reaction.

5 hours later, disappearance of the raw materials was confirmed by means of gas chromatography [TC-WAX (30 m); Temperature: 180°–200° C. (rise in temperature by 10° C. per 1 minute). After the solution was filtered through celite, the filtrate was washed with 1 L. of methanol and vacuum-concentrated. After the concentrate was solved in 2 L. of ether and washed with cold hydrochloric acid (0.5 mol/L.) and sequently with saturated sodium hydrogencarbonate and saturated brine, the solution was dried with magnesium sulfuric anhydride, and was concentrated to obtain 188 g of crude (Z)-2-tridecen-1-ol.

(Step 4)

Synthesis of (±)-cis-2,3-epoxy-1-tridecanol

A thermometer was mounted to a 5 L. four neck distillation flask for three one motor stirring.

Crude (Z)-2-tridecen-1-ol (188 g; 693 mmol) synthesized in the 3rd step and 3. 6 L. of methylene chloride were put into the flask and cooled to 5° C. After 187 g (net 131 g; 760 mmol) of m-chloroperbenzoic acid (70%) was added thereto for 30 minutes and then the temperature was gradually raised to room temperature, the mixture was stirred for 1 hour and a half.

After disappearance of the raw materials was confirmed by means of TLC (hexane.ethyl acetate=3:1), sodium thiosulfate.5 hydrate (199 g; 800 mmol) and sodium hydrogencarbonate (67 g; 800 mmol) solved in 1 L. of water were added thereto for 30 minutes and stirred for 1 hour to give an organic layer.

The organic layer was put together with a water layer extracted with 1 L. of methylene chloride and washed with saturated sodium hydrogencarbonate and then with saturated brine. After the solution was dried with magnesium sulfuric anhydride, 186 g of crude (±)-cis-2,3-epoxy-1-tridecanol was obtained by vacuum-concentration.

400 ml of hexane was added thereto to solve crystals at 60° C.

After the solution was left as it was for 15 hours at room temperature, the crystals were filtered and the filtrate was washed with cold hexane to give 107 g of (±)-cis-2,3-epoxy-1-tridecanol by vacuum drying at 40°–50° C.

The yield showed 72%.

Figure 2:
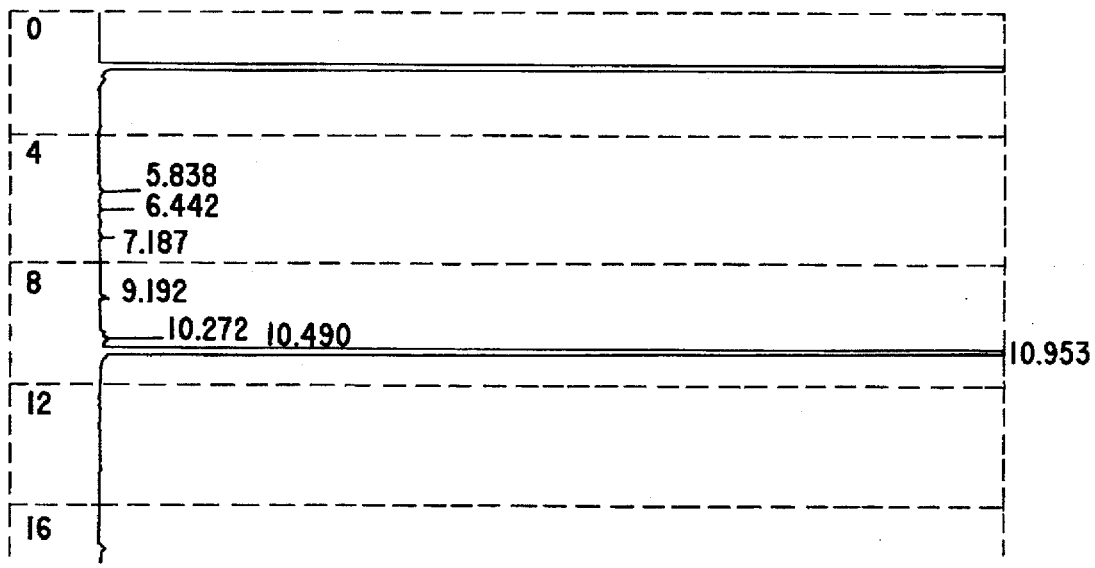
FIG. 2 is a chart showing gas-chromatography analysis of (±)-cis-2,3-epoxy-1-tridecanol obtained in the 4th step of the present invention.
Figure 3:
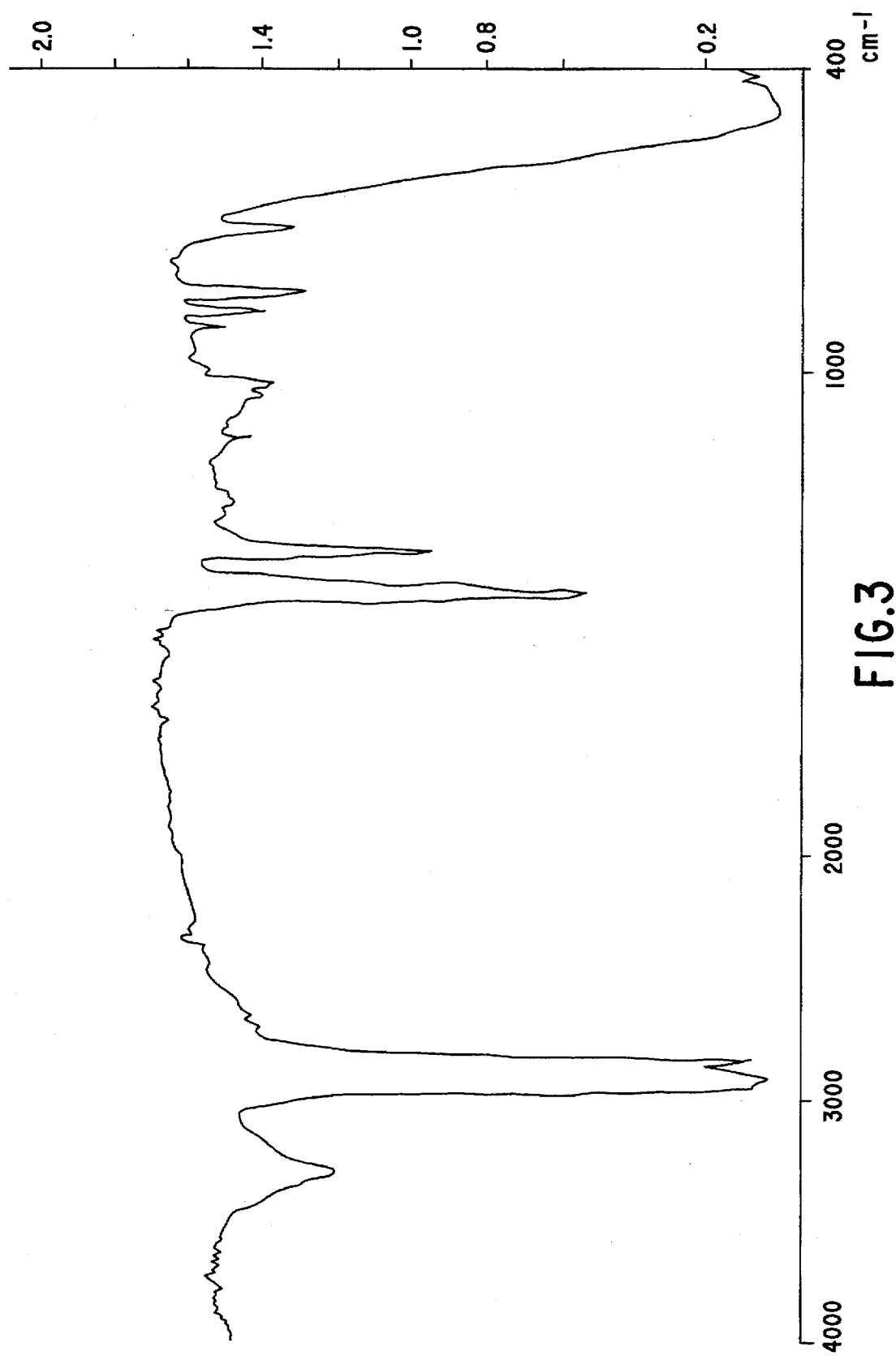
FIG. 3 is an infra red absorption spectrum of said (±)-cis-2,3-epoxy-1-tridecanol.
Figure 4:
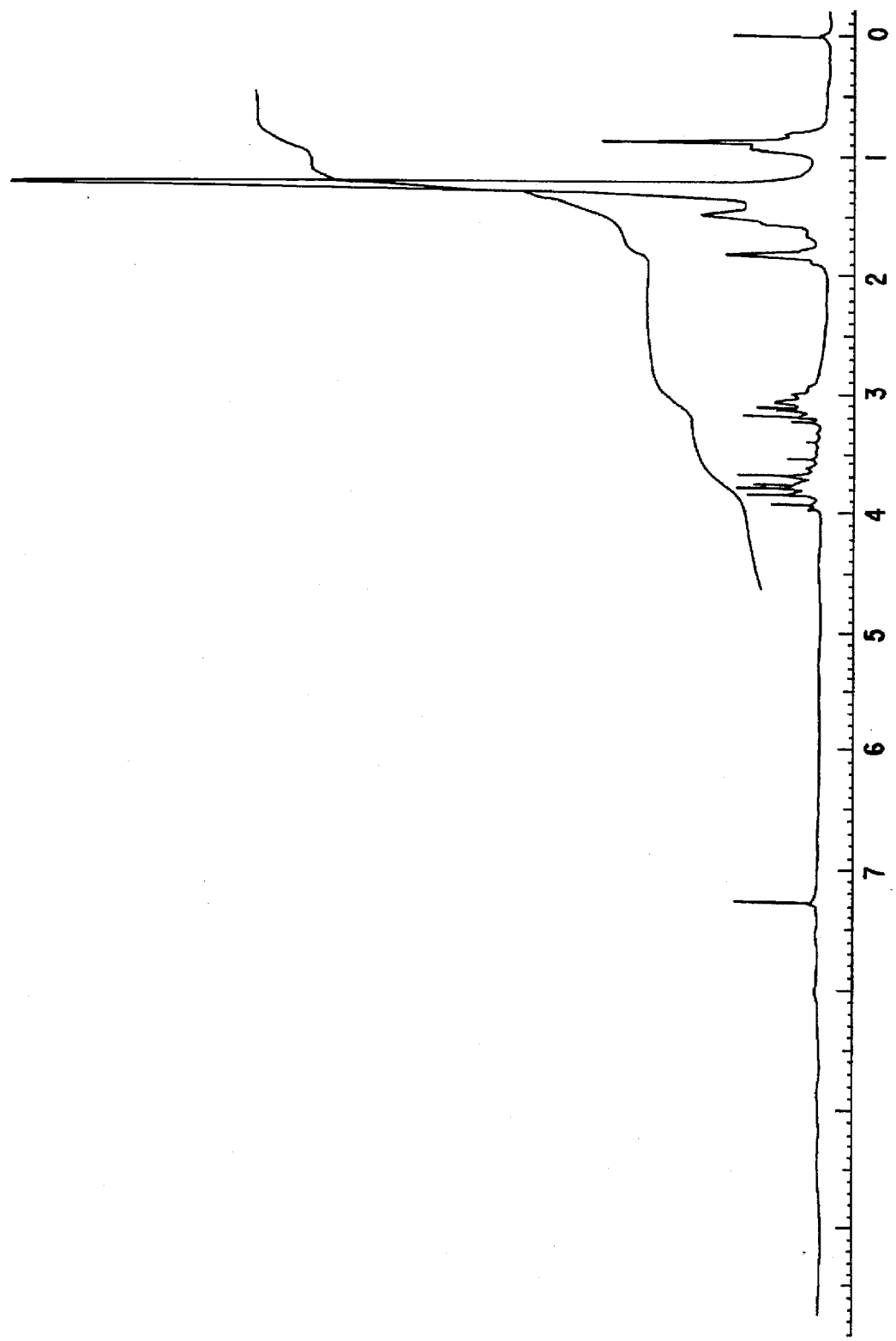
FIG. 4 is a proton nuclear magnetic resonance spectrum of said (±)-cis-2,3-epoxy-1-tridecanol.

The material synthesized in the 4th step was identified as (±)-cis-2,3-epoxy-1-tridecanol (purity: 96%) based on the analysis by means of gas chromatography [DB-1 (25cm); temperature: 100°–280° C. (rise in temperature by 10° C. per 1 minute)] (cf. FIG. 2), the infra red absorption spectra [IR] showing the absorption at wave lengths [vmax (cm$^{-1}$)] of 3,300, 2,920, 2,850, 1,460, 1,380 (cf. FIG. 3) and the δ values of the proton nuclear magnetic resonance spectra [NMR, σ(90 MHz, CDCl$_3$)] showing 0.88 (3H, t, J=5.5 Hz), 1.1–1.7 (18H, bm), 1.83 (1H, b), 2.9–3.2 (2H, m), 3.5–4.0 (2H, m) (cf. FIG. 4).

(Step 5)

Preparation of a large quantity of (2R,3S)-cis-2,3-epoxy-1-tridecanol 20 g (net 19.2 g; 90 mmol) of (±)-cis-2,3-epoxy-1-tridecanol (purity: 96%) was solved in 1 L. of diisopropyl ether and potassium hydrogencarbonate (9 g; 90 mmol) and acetic anhydride (9.2 g; 90 mmol) were added thereto. 20 g of lipase derived from pig pancreas (Trade name: Pancreatin F; Maker: Amano Pharmaceutical) was added to the solution and stirred with a magnetic stirrer at 20° C. The transformation ratio of the reaction was observed by sampling hourly by means of gas chromatography (TC-WAX (30m); Temperature: 220° C.-fixed).

The solution was still stirred for 1 hour after the transformation ratio had exceeded 60% 8 hours later from the start of the reaction, and then the stirring was stopped and the solution was suction-filtered.

The filtrate was washed out with ether and an organic layer was mixed therewith. The mixture was washed with saturated sodium hydrogencarbonate and then with saturated brine, and dried with magnesium sulfuric anhydride to give crude (2R,3S)-cis-2,3-epoxy-1-tridecanol by vacuum-concentration. 130 ml of hexane was added thereto to solve crystals at 60 ° C. The solution was left as it was at 5° C. for 1 hour and washed with cold hexane after filtration of the crystals. The washed solution was vacuum-dried at 40°–50° C. to give 5.10 g of (2R,3S)-cis-2,3-epoxy-1-tridecanol.

The yield shown by gas chromatography [DB-1 (25cm); Temperature: 100°–280° C. (rise in temperature by 10° C. per 1 minute)] was 27% (cf. FIG. 5). At 98% of purity melting point was 60° C., [α]$_D$ equaled −7.96° (EtOH, c=0.995), and the results of IR and NMR analyses were as same as these of the racemic modification obtained in the 4th step.

Determination of optical purity of (2R,3S)-cis-2,3-epoxy-1-tridecanol

About 30mg of (2R,3S)-cis-2,3-epoxy-1-tridecanol was solved in 0.5 ml of ether, and about 0.05 ml of pyridine was added thereto. About 20mg of benzoyl chloride was added thereto and stirred for 30 minutes at room temperature. 1 ml of ether was added to the reactant and washed with saturated aqueous solution of copper sulfate and then with water to be dried with sodium sulfuric anhydride. After concentration, the residue was purified by means of silica gel column chromatography (1 g; hexane.ether=10:1) to give benzoate.

Benzoate corresponding to racemic epoxy alcohol [(±)-cis-2,3-epoxy-1-tridecanol] was obtained in the same manner described above.

Figure 6:
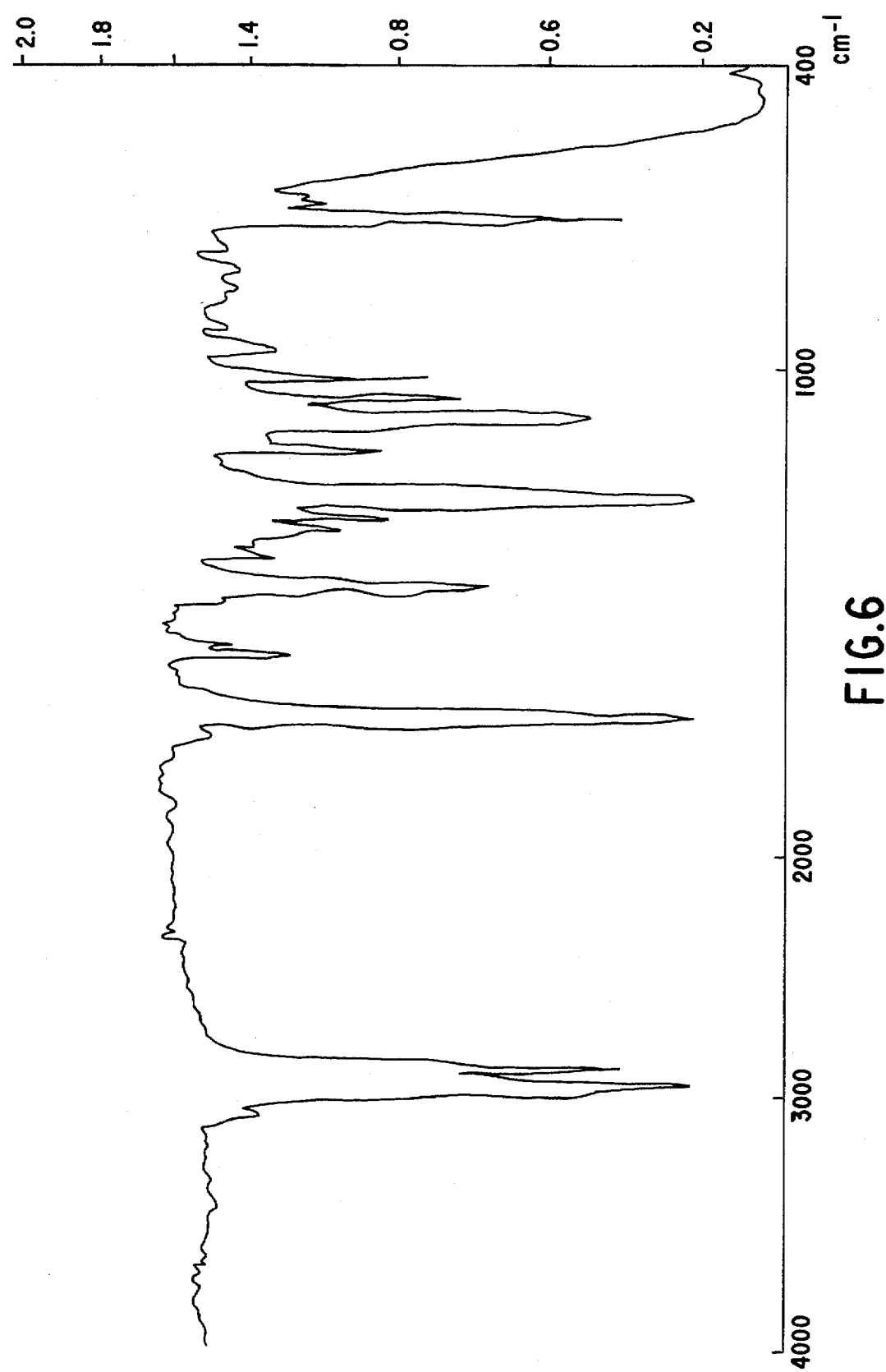
FIG. 6 is an infra red absorption spectrum of (±)-cis-2,3-epoxy-1-tridecanol benzoate obtained in the 5th step of the present invention.

The infra red absorption spectra (IR) of the obtained benzoate [(±)-cis-2,3-epoxy-1-tridecanol benzoate] showed the absorption at wave lengths [v max (cm$^{-1}$)] of 3,060, 2,920, 2,850, 1,720, 1,600, 1,580, 1,495, 1,450, 1,110, 1,070, 1,030, 720 (cf. FIG. 6).

Both were analyzed by means of optically active HPLC [Clumn (trade name): Chiralcel OJ; Maker: Dicell Chemical Industries; 4.6 mm ×250 mm; Eluate: hexane/2-propanol (1000/3); Detection: 254 nm; Rate of flow: 1 ml/minute; Temperature: room temperature; Period for keeping: (2R, 3S)-form -10 minutes, (2S,3R)-form -13 minutes].

Figure 7:
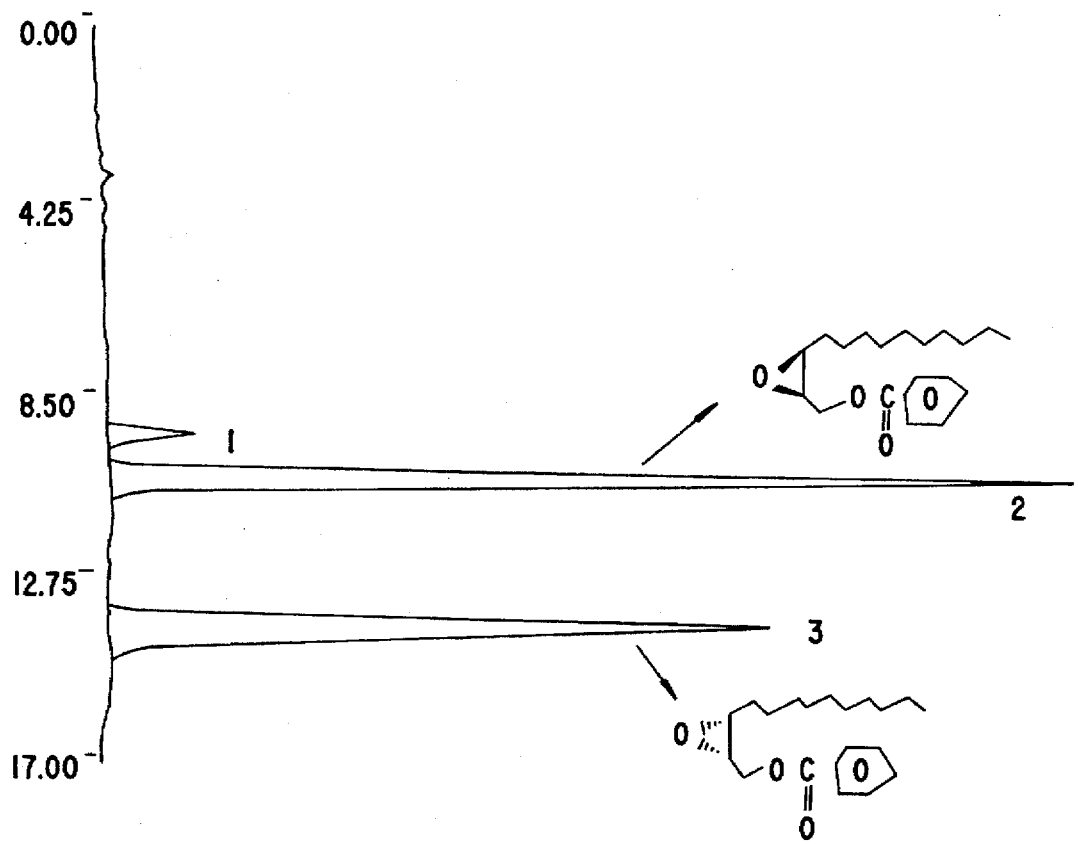
FIG. 7 is a chart showing HPLC analysis of said (±)-cis-2,3-epoxy-1-tridecanol benzoate.
Figure 8:
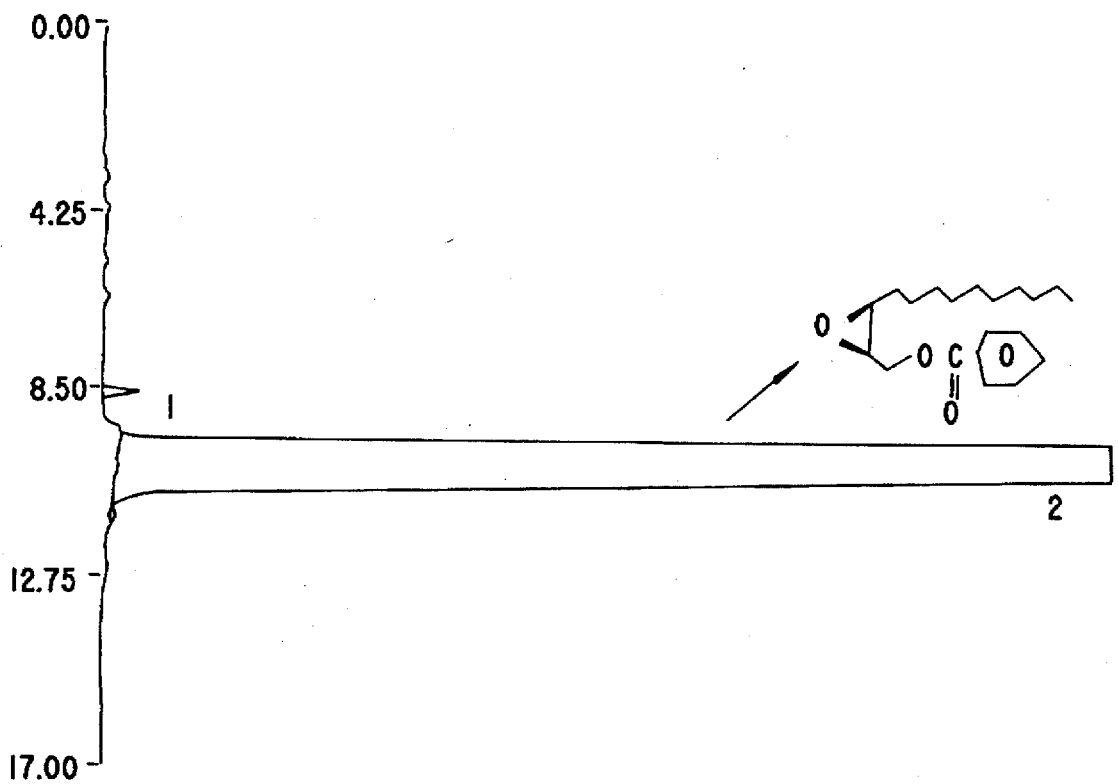
FIG. 8 is a chart showing HPLC analysis of (2R,3S)-cis-2,3-epoxy-1-tridecanol benzoate obtained in the 5th step of the present invention.

The analyses of (±)-cis-2,3-epoxy-1-tridecanol benzoate and (2R,3S)-cis-2,3-epoxy-1-tridecanol benzoate were respectively shown in FIG. 7 and 8.

(Step 6)

Synthesis of (2R,3S)-cis-2,3-epoxy-1-tridecanyltosylate 4.7 g (net 4.6 g; 22 mmol) of (2R,3S)-cis-2,3-epoxy-1-tridecanol (98%) was solved in 50 ml of pyridine and cooled to 10° C.

6.2 g (32 mmol) of p-toluenesulfonylchloride was added thereto for 15 minutes and was stirred for 6 hours at freezing temperature. After disappearance of the raw materials was confirmed by TLC (hexane.ethyl acetate=4:1), ether (300 ml) was added.

The reactant was washed with cold hydrochloric acid (0.5 mmol/L.), with saturated sodium hydrogencarbonate and then with saturated brine. The washed solution was dried with sodium sulfate anhydride and concentrated. The residue was purified with silica gel chromatography (130 g; hexane.ethyl acetate=10:1) to give 6.2 g of tosylate (yield: 78%).

Figure 9:
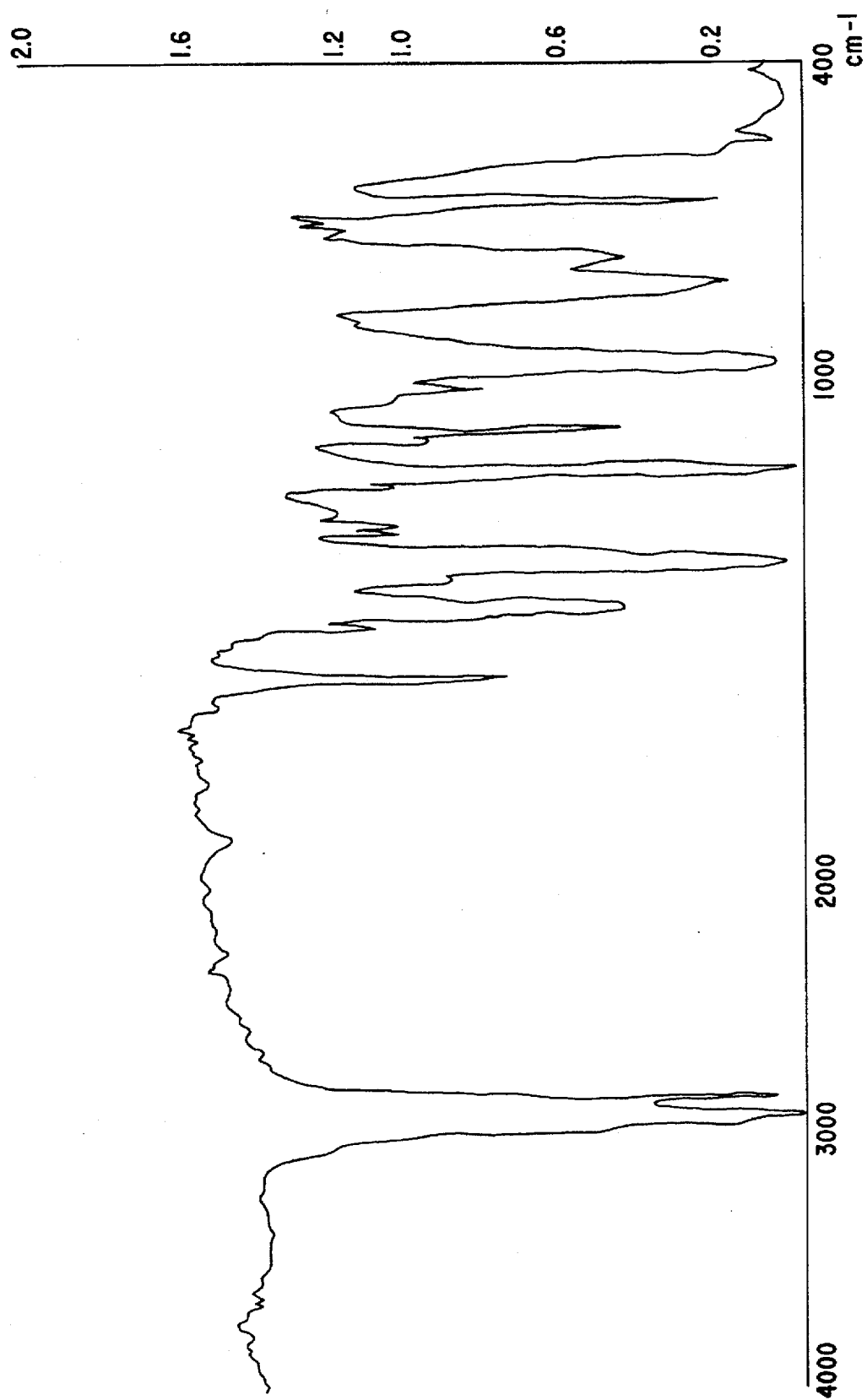
FIG. 9 is an infra red absorption spectrum of (2R,3S)-cis-2,3-epoxy-tridecanyltosylate obtained in the 6th step of the present invention.

The obtained tosylate was identified as (2R,3S)-cis-2,3-epoxy-tridecanyl tosylate based on the infra red absorption spectra (IR) showing the absorption at wave lengths [ν max (cm⁻¹)] of 3,070, 2,920, 2,850, 1,600, 1,500, 1,460, 1,370, 1,180, 1,120, 1,100, 1,020, 980, 820, 780, 680 (cf. FIG. 9).

Preparation of 4-methylpentyl lithium

A thermometer, a Dimroth condenser to which an argon baloon was mounted at the upper portion and an isobaric dropping funnel were mounted to 100 ml three neck distillation flask for stirring with a magnetic stirrer.

After substitution inside the flask with argon, 1.4 g (200 mmol) of lithium was cut into pieces and put into the flask. 5 ml of dry ether and 0.5 ml of 1-bromo-4-methylpentane was added thereto to start a reaction. After the reactant was cooled to 10° C., 11 g (67 mmol) of 1-bromo-4-methylpentane solved in 50 ml of dry ether was dropped for 30 minutes. The reaction temperature was controlled under 15° C. After the drop was finished, the solution was stirred for 1 hour at from 5° to 10° C. The solution was left as it was for 1 hour after the stirring was stopped and then was titrated.

Titration of 4-methylpentyl lithium

A very small quantity of o-phenanthroline and 2 ml of dry ether were put into 20 ml sample tube and substituted with argon. Septum rubber was mounted thereto and a disposable injection needle was slicked. The prepared 4-methylpentyl lithium solution (1 ml) was added through the injection and showed a color reaction of reddish brown.

As a titration reagent sec-BuOH toluene solution (1 mmol/L.) was dropped and the concentration was calculated. The average value was founded by the culculation at n=3 in the same manner [Concentration=amount of sec-BuOH (ml) /amount of sample (1 ml)].

Thus the concentration of 4-methylpentyl lithium reagent was determined as 1 mol/L..

Preperation of di(4-methylpentyl) lithium copper

A thermometer, a Liebig condenser to which an argon baloon was mounted at the upper portion and an isobaric dropping funnel were mounted to 100 ml three neck distillation flask for stirring with a magnetic stirrer.

After substitution inside the flask with argon, 3.81 g (20 mmol) of copper iodide (95%) and 20 ml of dry diethylether were added and stirred. The obtained suspension was cooled to –30° C., and then 40 ml (40 mmol) of the above prepared 4-methylpentyl lithium solution (1 mol/L.) was dropped thereto at temperature controlled under –15° C. The concentration of the obtained di(4-methylpentyl) lithium copper reagent was 0.3 mol/L..

(Step 7)

Synthesis of (7R,8S)-cis-2-methyl-7,8-epoxyoctadecane

A thermometer, a Liebig condenser to which an argon baloon was mounted at the upper portion and an isobaric dropping funnel were mounted to 100 ml three neck distillation flask for stirring with a magnetic stirrer.

After substitution inside the flask with argon, 3.0 g (8.2 mmol) of (2R,3S)-cis-2,3-epoxy-tridecanyltosylate obtained in the 6th step and 30 ml of dry ether were added and cooled to –60° C. 30 ml (9 mol) of decyl lithium copper reagent (0.3 mol/L.) was dropped into the solution at temperature under –50° C. After the drop was finished, the solution was stirred for 1 hour at from –60°to –50° C. Disapperance of the raw materials was confirmed by TLC (hexane.ethyl acetate= 10:1) and then 20 ml of saturated ammonium solution was dropped for conclusion of the reaction. After the temperature rose to room temperature, the reactant was filtered through celite and the celite was washed out with ether.

Organic layer was washed with saturated brine and dried with magnesium sulfuric anhydride to be concentrated.

The concentrate was purified through silica gel column chromatography [100 g, pentane: ether=100:1–50:1] to yield 1.8 g of the objective (yield: 78%).

Figure 10:
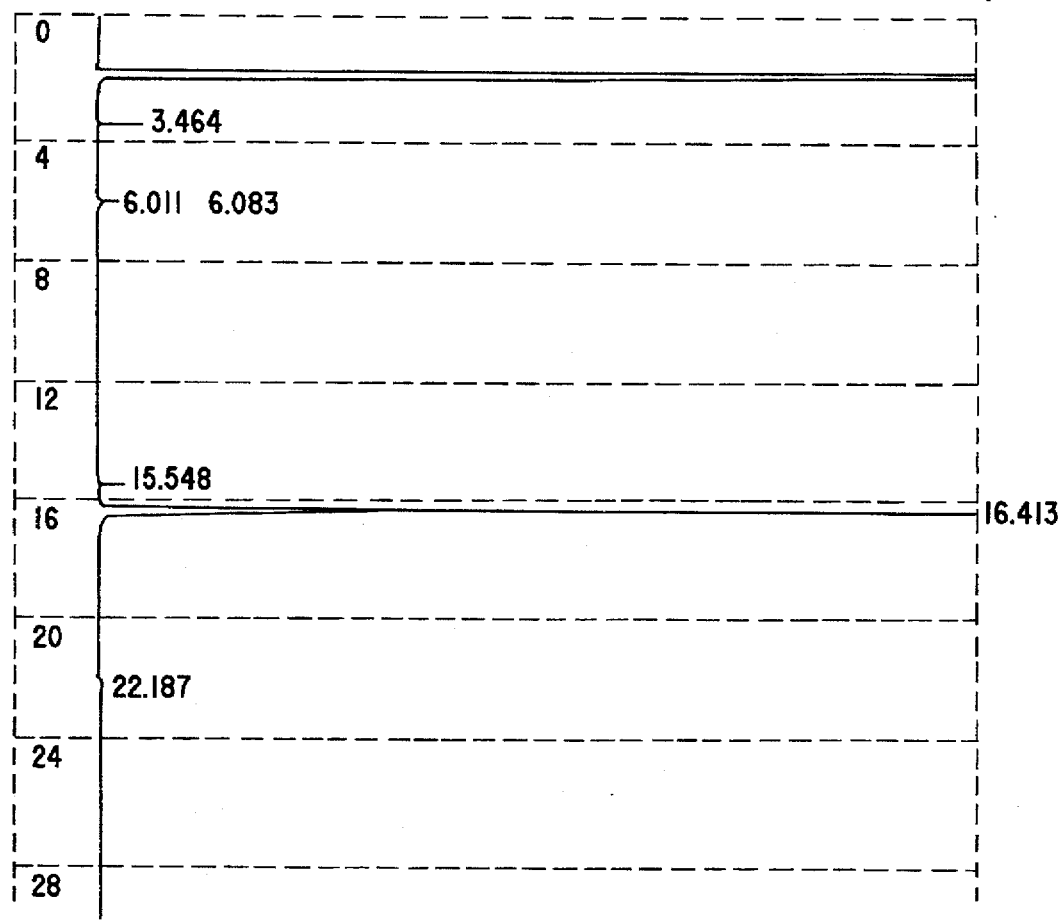
FIG. 10 is a chart showing gas-chromatography analysis of (7R,8S)-cis-2-methyl-7,8-epoxyoctadecane obtained in the final step of the present invention.
Figure 11:
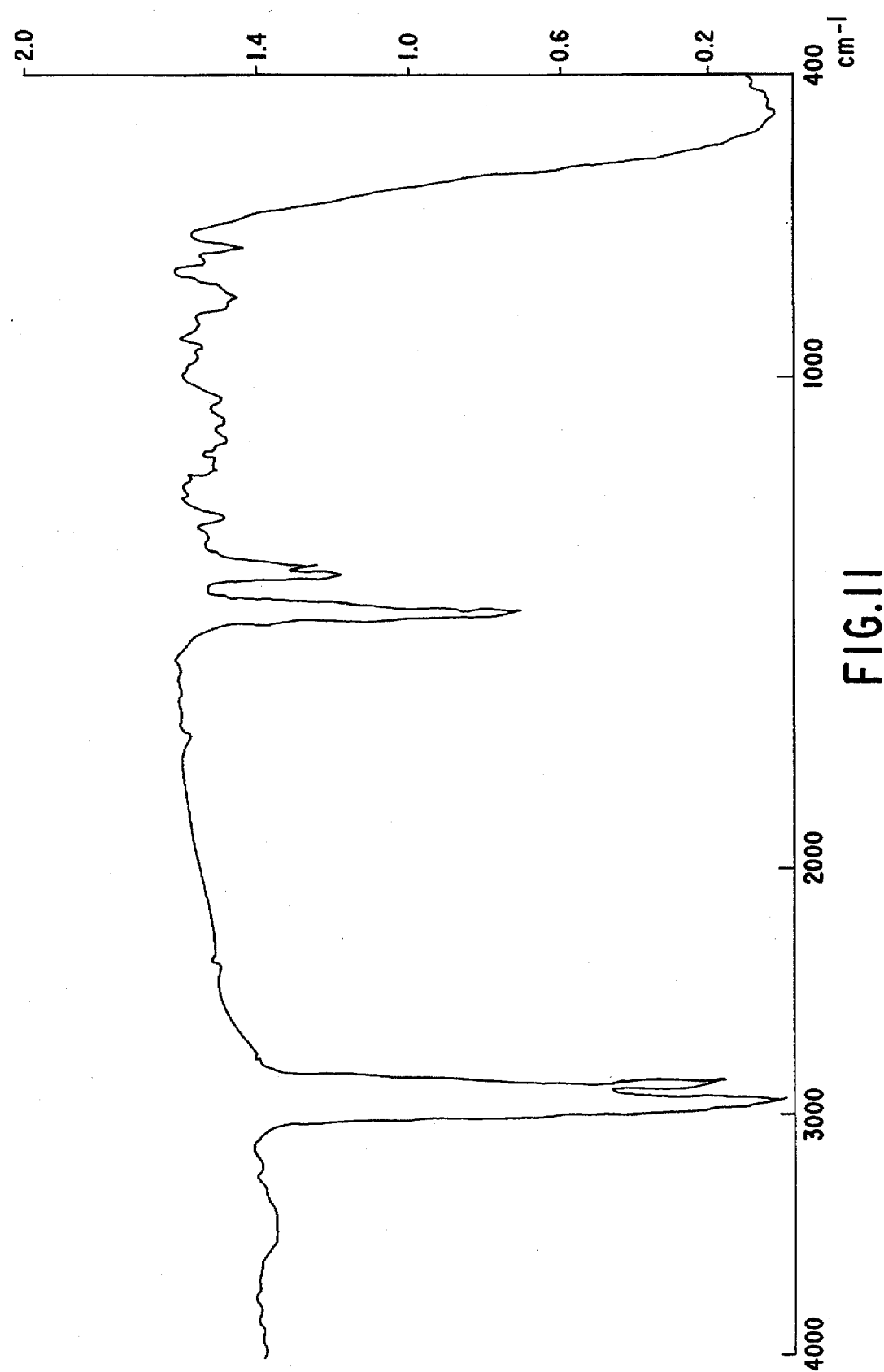
FIG. 11 is an infra red absorption spectrum of said (7R,8S)-cis-2-methyl-7,8-epoxyoctadecane.
Figure 12:
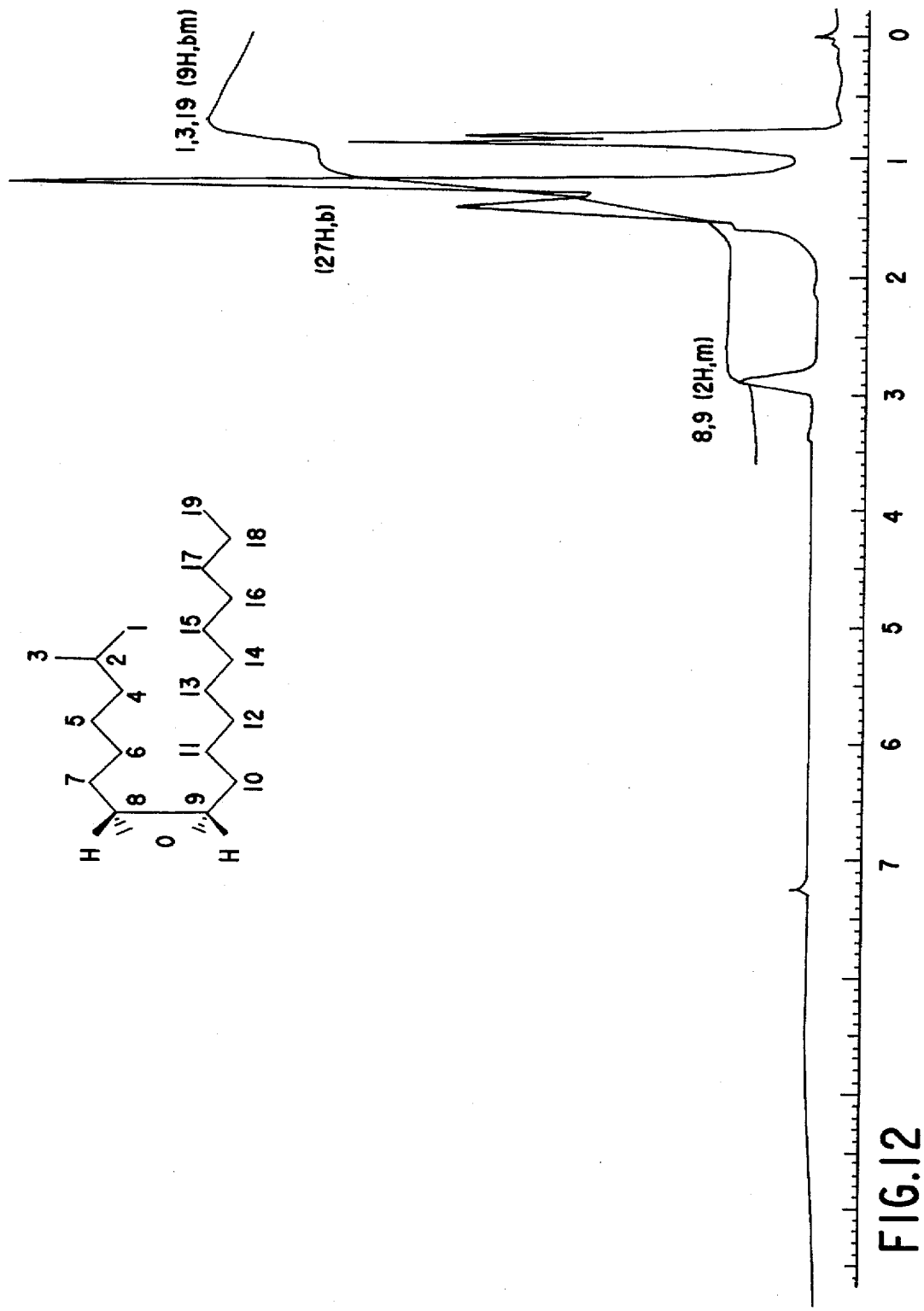
FIG. 12 is a proton nuclear magnetic resonance spectrum of said (7R,8S)-cis-2-methyl-7,8-epoxyoctadecane.

The synthesized material was identified as (7R,8S)-cis-2-methyl-7,8-epoxyoctadecane (purity: 96.72) which is the sex pheromone of Lymantria dispar L. based on the analysis by means of gas chromartography [DB-1 (30m); Temperature: 100° C. (2 minutes)–250° C. (rise in temperature by 10° C. per 1 minute); Period for keeping: 16 minutes] (cf. FIG. 10), the infra red absorption spectra (IR) showing the absorption at wave lengths [ν max (cm⁻¹)] of 2,950, 2,920, 2,850, 1,460, 1,380, 1,360, 820 (cf. FIG. 11), and the δ values of the proton nuclear magnetic resonance spectra [NMR, σ(90 MHz, CDCl₃)] showing 0.7–1.0 (9H, bm), 1.1–1.8 (27H, bm), 2.7–3.0 (2H, b) (cf. FIG. 12).

(Test)

The attractive effect of the above obtained sex pheromone of Lymantria dispar L. was confirmed by test described below.

0.5 mg of the above obtained (7R,8S)-cis-2-methyl-7,8-epoxyoctadecane, the sex pheromone of Lymantria dispar L., solved in 0.05 ml of hexane was absorbed into a septum rubber and put on an adhesive trap (15 cm ×30 cm) in the center. Then the adhesive trap was set at a golf link where Lymantria dispar L. was breeding.

Two hours later from the setting, the number of Lymantria dispar L. catched at the trap was 65.

As a control, an adhesive trap on which only a septum rubber was put was set in the same manner and the number of Lymantria dispar L. catched at the trap was 5.

Thus the attractive effect of the above obtained sex pheromone of Lymantria dispar L. was confirmed.

What is claimed is:

1. A process for preparing, (7R,8S)-cis-2-methyl-7,8-epoxyoctadecane, the sex pheromone of Lymantria dispar L., which comprises: reacting 1-bromodecane

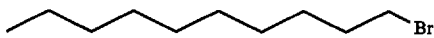

and propargyl alcohol tetrahydropyranylether

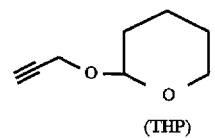

(THP)

in the presence of sodium hydroxide to give 1-tetrahydropyranyloxy-2-tridecyne

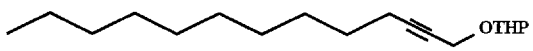

treating said 1-tetrahydropyranyloxy-2-tridecyne with p-toluenesulfonic acid to give 2-tridecyn-1-ol

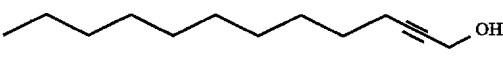

catalytically-hydrogenating said 2-tridecyn-1-ol in the presence of Lindlar catalyst to give (Z)-2-tridecen-1-ol

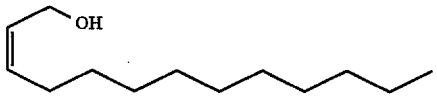

oxidizing said (Z)-2-tridecen-1-ol with a peroxide selected from the group consisting of m-chloroperbenzoic acid, monomagnesium monoperphthalate and t-butyl peroxide to give (±)-cis-2,3-epoxy-1-tridecanol

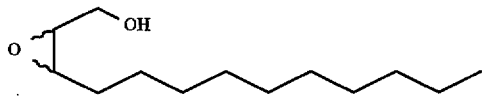

stereoselectively acylatating said (±)-cis-2,3-epoxy-1-tridecanol with an acid anhydride in an organic solvent and in the presence of a lipase, and after acylation recovering unreacted optically active (2R,3S)-cis-2,3-epoxy-1-tridecanol

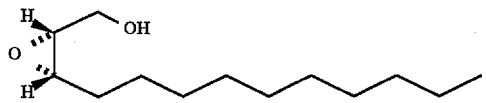

reacting said optically active (2R,3S)-cis-2,3-epoxy-1-tridecanol with p-toluenesulfonylchloride to give (2R,3S)-cis-1-p-toluenesulfoxy-2,3-epoxytridecane

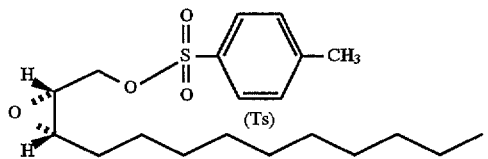

and reacting said (2R,3S)-cis-1-p-toluenesulfoxy-2,3-epoxytridecane with di(4-methylpentyl) lithium copper reagent to yield (7R,8S)-cis-2-methyl-7,8-epoxyoctadecane

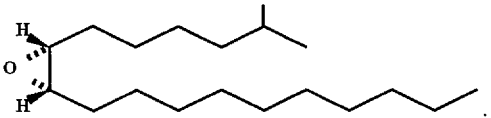

2. A process for preparing the sex pheromone of *Lymantria dispar L.* as set forth in claim 1, wherein said peroxide is m-chloroperbenzoic acid.

3. A process for preparing the sex pheromone of *Lymantria dispar L.* as set forth in claim 2, wherein said lipase is selected from the group consisting a lipase derived from pancreas of pig, a lipase derived from bacteria, a lipase derived from yeast and a lipase derived from mold.

4. A process for preparing the sex pheromone of *Lymantria dispar L.* as set forth in claim 2, wherein said lipase is a lipase derived from pig pancreas.

5. A process for preparing the sex pheromone of *Lymantria dispar L.* as set forth in claim 2, wherein said organic solvent is diisopropylether.

6. A process for preparing the sex pheromone of *Lymantria dispar L.* as set forth in claim 5, wherein said lipase is selected from the group consisting a lipase derived from pancreas of pig, a lipase derived from bacteria, a lipase derived from yeast and a lipase derived from mold.

7. A process for preparing the sex pheromone of *Lymantria dispar L.* as set forth in claim 5, wherein said lipase is a lipase derived from pig pancreas.

8. A process for preparing the sex pheromone of *Lymantria dispar L.* as set forth in claim 1, wherein said organic solvent is diisopropylether.

9. A process for preparing the sex pheromone of *Lymantria dispar L.* as set forth in claim 8, wherein said lipase is selected from the group consisting a lipase derived from pancreas of pig, a lipase derived from bacteria, a lipase derived from yeast and a lipase derived from mold.

10. A process for preparing the sex pheromone of *Lymantria dispar L.* as set forth in claim 8, wherein said lipase is a lipase derived from pig pancreas.

11. A process for preparing the sex pheromone of *Lymantria dispar L.* as set forth in claim 1, wherein said lipase is selected from the group consisting a lipase derived from pancreas of pig, a lipase derived from bacteria, a lipase derived from yeast and a lipase derived from mold.

12. A process for preparing the sex pheromone of *Lymantria dispar L.* as set forth in claim 1, wherein said lipase is a lipase derived from pig pancreas.

* * * * *

UNITED STATES PATENT AND TRADEMARK OFFICE
CERTIFICATE OF CORRECTION

PATENT NO.:    5,677,155
DATED      :    Oct. 14, 1997
INVENTOR(S):   Fukusaki et al.

Figure 5:
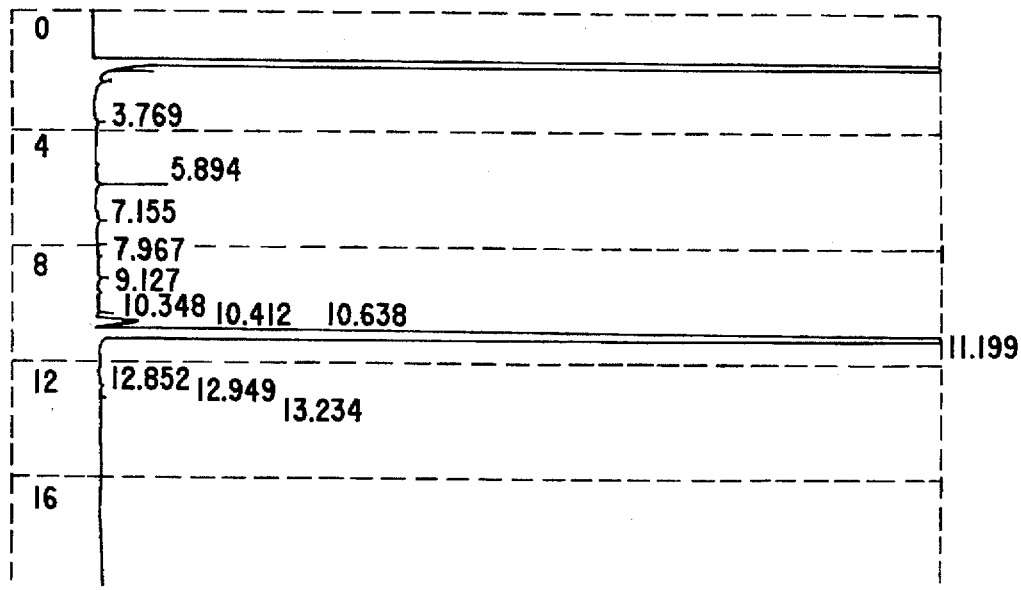
FIG. 5 is a chart showing gas-chromatography analysis of (2R,3S)-cis-2,3-epoxy-1-tridecanol obtained in the 5th step of the present invention.

It is certified that errors appear in the above-identified patent and that said Letters Patent is hereby corrected as shown below:

Fig. 1,    correct "DIISOPROPYL EHTER" to --DIISOPROPYL ETHER--;
Fig. 5,    top line, before "CHRMI" add the symbol " Ĉ ";

Fig. 7, 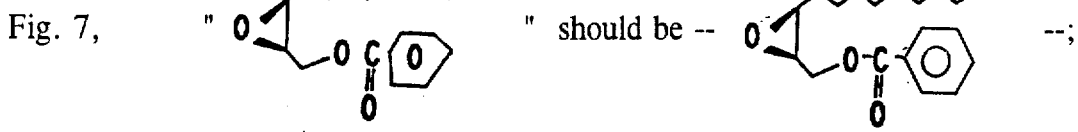

Fig. 7, 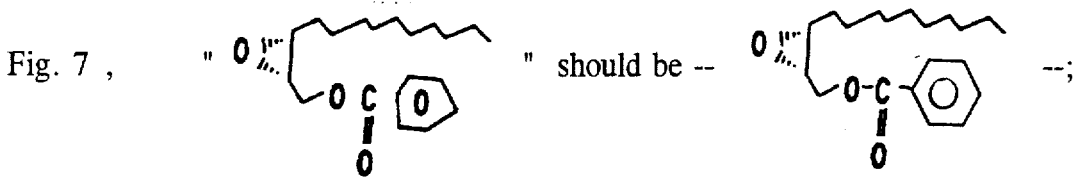

Fig. 8, 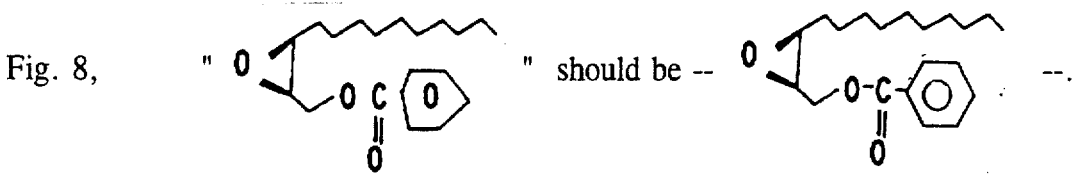

Signed and Sealed this

Twenty-sixth Day of May, 1998

Attest:

BRUCE LEHMAN

Attesting Officer    Commissioner of Patents and Trademarks